US005637310A

United States Patent [19]
Johnson

[11] Patent Number: 5,637,310
[45] Date of Patent: *Jun. 10, 1997

[54] METHOD OF TREATING PROSTATIC ADENOCARCINOMA

[75] Inventor: Randall K. Johnson, Ardmore, Pa.

[73] Assignee: SmithKline Beecham Corporation, King of Prussia, Pa.

[*] Notice: The term of this patent shall not extend beyond the expiration date of Pat. No. 5,300,294.

[21] Appl. No.: 452,765

[22] Filed: May 30, 1995

Related U.S. Application Data

[63] Continuation of Ser. No. 170,481, Dec. 20, 1993, Pat. No. 5,496,556.

[51] Int. Cl.$^6$ .............. A61F 2/02; A61K 9/20; A61K 31/56; A61K 31/58
[52] U.S. Cl. .............. 424/423; 424/451; 424/456; 424/464; 514/169; 514/172; 514/173; 514/177; 514/178; 514/179; 514/180; 514/181; 514/182; 514/319; 514/428; 514/462
[58] Field of Search .............. 424/423, 451, 424/456, 464; 514/169, 172, 173, 177, 178, 179, 180, 181, 182, 319, 428, 462

[56] References Cited

U.S. PATENT DOCUMENTS

| | | | |
|---|---|---|---|
| 4,882,319 | 11/1989 | Holt et al. | 514/119 |
| 4,910,226 | 3/1990 | Holt et al. | 514/319 |
| 4,937,237 | 6/1990 | Holt et al. | 514/75 |
| 4,946,834 | 8/1990 | Holt et al. | 514/135 |
| 4,970,205 | 11/1990 | Holt et al. | 514/173 |
| 5,017,568 | 5/1991 | Holt et al. | 514/173 |
| 5,032,586 | 7/1991 | Holt et al. | 514/177 |
| 5,041,433 | 8/1991 | Holt et al. | 514/176 |
| 5,137,882 | 8/1992 | Holt et al. | 514/182 |

FOREIGN PATENT DOCUMENTS

| | | |
|---|---|---|
| 0004949B1 | 4/1978 | European Pat. Off. . |
| 200859 | 11/1986 | European Pat. Off. . |
| 279010 | 8/1988 | European Pat. Off. . |
| 0285383A2 | 10/1988 | European Pat. Off. . |
| 414490A | 2/1991 | European Pat. Off. . |
| 414491A | 2/1991 | European Pat. Off. . |
| 9100733 | 1/1991 | WIPO . |

OTHER PUBLICATIONS

J. Natl Cancer Inst; 74(2) pp. 475–486 (1985).
The Urologic Clinics of North America; vol. 18, No. 1 pp. 93–98 (1991).
Progress in Cancer Research Therapy; vol. 31, No. 2 pp. 477–489 (1984).
J. Med. Chem.; vol. 33, No. 3, pp. 937–942 (1990).
J. Med. Chem.; vol. 33, No. 3, pp. 943–950 (1990).
J. Steroid Biochem; vol. 34, Nos. 1–6, pp. 571–575 (1989).
The Prostate; 18, pp. 215–227 (1991).
J. Steroid Biochem; 24, pp. 887–886 (1986).
Bio Chemistry; 28, pp. 140–148 (1989).
Endocrinology, 117 No. 2, pp. 571–579 (1985).
Academic Press, Inc, CH 8 V, pp. 269–304 (1984).

*Primary Examiner*—Carlos Azpuru
*Attorney, Agent, or Firm*—Wayne J. Dustman; Charles M. Kinzig; Edward T. Lentz

[57] ABSTRACT

Invented is a Method of Treating Prostatic Adenocarcinoma by employing asteroid 5-α-reductase inhibiting compound or a combination of steroid 5-α-reductase inhibiting compounds.

2 Claims, No Drawings

METHOD OF TREATING PROSTATIC ADENOCARCINOMA

This is a continuation of application Ser. No. 08/170,481, filed 20 Dec. 1993 now U.S. Pat. No. 5,496,556.

This invention relates to a method of treating prostatic adenocarcinoma by employing asteroid 5-α-reductase inhibiting compound. Advantageously the method of this invention employs 17β-(N-t-butylcarboxamide)-androst-3,5-diene-3-carboxylic acid in the symptomatic relief of prostatic adenocarcinoma.

BACKGROUND OF THE INVENTION

The class of steroidal horomones known as androgens is responsible for the physical characteristics that differentiate males from females. Of the several organs that produce androgens, the testes produce these hormones in the greatest amounts. Centers in the brain exert primary control over the level of androgen production. Numerous physical manifestations and disease states result when ineffective production control results in excessive androgen hormone production. For example, ache vulgaris, seborrhea, female hirsutism, and benign prostatic hypertrophy are correlated with elevated androgen levels. Additionally, the incidence of male pattern baldness has been associated with high androgen levels.

Testosterone is the principal androgen secreted by the testes and is the primary androgenic steroid in the plasma of males. It now is known that 5-α-reduced androgens are active hormones in some tissues such as the prostate and sebaceous gland. Circulating testosterone thus serves as a prohormone for dihydrotestosterone (DHT), its 5-α-reduced analogue in these tissues but not in others such as muscle and testis. Steroid 5-α-reductase is a NADPH-dependent enzyme that converts testosterone to DHT. The importance of this enzyme in male development was dramatically underscored by discovery of a genetic steroid 5-α-reductase deficiency in male pseudohermaphrodites. Imperato-McGinley, J., et al., (1979), *J. Steroid Biochem.* 11:637–648.

Recognition of the importance of elevated DHT levels in various disease states has stimulated many efforts to synthesize inhibitors of this enzyme.

The first inhibitor described was 4-androsten-3-one-17β-carboxylic acid by Hisa and Voight in 1973. *J. Invest. Dermat.* 62:224–227. (4R)-5,10-seco-19-norpregna-4,5-diene-3,10,20-triane was the next inhibitor to be described and also has found utiltiy as an affinity label for 5-α-reductase. Robaire, B., et al., (1977), *J. Steroid Biochem.* 8:307–310. (5α,20-R)-4-diazo-21-hydroxy-20-methlypregnan-3-one has been reported as a potent, time-dependent inhibitor of steroid 5-α-reductase. Blohm, T. R., et al., (1980), *Biochem. Biophys. Res. Comm.* 95:273–280; U.S. Pat. No. 4,317,817, Mar. 2, 1982. 17β-N, N-diethylcarbomoyl-4-methyl-4-aza-5-α-androstan-3-one is exemplary of a group of 4-aza steroid inhibitors of steroid 5-α-reductase described in U.S. Pat. No. 4,377,584 which issued Mar. 22, 1983, and in Liang, T., et al., (1983), *J. Steroid Biochem.* 19, 385–390. 17α-acetoxy-6-methylenepregn-4-ene-3,20-dione also has been shown to be a time-dependent inactivator of steroid 5-α-reductase. Petrow, V., et al., (1981), *Steroids* 38:121–140.

Other steroid 5-α-reductase inhibitors also have been described. U.S. Pat. No. 4,361,578 which issued Jun. 2, 1986, describes a class of homosteroid enzyme inhibitors. U.S. Pat. No. 4,191,759 discloses amides of 17β-carboxy-4-androsten-3-one that are active as steroid 5-α-reductase inhibitors. Japanese Patents J60146855-A and J60116657-A disclose various aniline derivatives having numerous activities including 5-α-reductase inhibiting activity. Japanese Patent 60142941-A discloses phenyl-substituted ketones having 5-α-reductase inhibiting activity and European Patent EP173516-A discloses various phenyl-substituted amides having similar activity. Shiseido referenced terpene derivatives that are active inhibitors of steroid 5-α-reductase. Japanese Patent J59055417-A.

It has been postulated but never proven that the inhibition of steroid 5-α-reductase would result in a therapeutic effect on prostatic adenocarcinoma in mammals, *Novel Approaches to Cancer Chemoterapy*, Pub: Academic Press, Inc. (1984) Ch.8 V. Petrow and G. Padilla 5-α-reductase: A target enzyme for Prostatic Cancer, however, contrary evidence has also been published, Liang, t., et al., (1985), *Endocrinology* 117, No. 2: 571–579.

It has now been discovered that steroid 5-α-reductase inhibitors do have a therapeutic effect on prostatic adenocarcinoma of mammals.

SUMMARY OF THE INVENTION

The present invention resides in the discovery that steroid 5-α-reductase inhibiting compounds have a therapeutic effect on prostatic adenocarcinoma.

Included in the present invention are combinations of steriod 5-α-reductase inhibitors and pharmaceutical compositions comprising a pharmaceutical carrier and a compound or a combination of compounds useful in the method of the invention.

DESCRIPTION OF THE INVENTION

An inhibitor of steriod 5-α-reductase or a combination of inhibitors of steroid 5-α-reductase are used in a pharmaceutical composition to treat prostatic adenocarcinoma.

Also included are derivatives of these compounds which may either give rise to the parent compounds in vivo or be useful themselves, such as pharmaceutically acceptable addition salts. Salts of these compounds containing a basic group are formed with organic or inorganic acids in the presence of a basic compound by methods known to the art. For example, the compound is reacted with an inorganic or organic acid in an aqueous miscible solvent such as ethanol with isolation of the salt by removing the solvent or in an aqueous immiscible solvent when the acid is soluble therein, such as ethyl ether or chloroform, with the desired salt separating directly or isolated by removing the solvent. Examplary of the acid addition salts which are included in this invention are maleate, fumarate, lactate, oxalate, methane sulfonate, ethanesulfonate, benzenesulfonate, tartrate, citrate, hydrochloride, hydrobromide, sulfate, phosphate and nitrate salts. Pharmaceutically acceptable base addition salts of compounds of the invention containing an acidic group are prepared by known methods from organic and inorganic bases include nontoxic alkali metal and alkaline earth bases, for example, calcium, sodium, and potassium hydroxide; ammonium hydroxide, and nontoxic organic bases such as triethylamine, butylamine, piperazine, and (trihydroxymethly)methylamine. Prodrug derivatives include 0-esters, especially the tri-0-lower alkanoly ester having from 2–8 carbon atoms in each alkanoyl group; 0-methly ethers or sulfate esters. Separated R and S stereoisomers are also useful.

Compounds that are considered to be steroid 5-α-reductase inhibitors include:
17β-(N-t-butylcarboxamide)-5-α-androst-1-ene-4-aza-3-one, (20R)-hydroxymethyl-4-methyl-4-aza-5-alphapregnane-3-one, 17β-(N,N-diisopropylcarboxamide)-5-α-8(14)-androsten-4-methyl-4-aza-3-one, 17β-(N-t-butylcarboxamide)-5-α-8(14)-androsten-4-methyl-4-aza-3-one, 17β-(N,N-diisopropylcarboxamide)-3-nitro-5-α-androst-3-ene, 17β-(N-t-butylcarboxamide)-3-nitro-5-α-androst-3-ene, 17β-(N,N-diisopropylcarboxamide)-3-nitro-5-α-androst-2-ene, 17β-(N-t-butylcarboxamide)-androst-3,5-diene-3-carboxylic acid or a salt thereof, 17β-(N,N-diisopropylcarboxamide)-androst-3,5-diene-3-carboxylic acid or a salt thereof, 17β-(N,N-diisopropylcarboxamide)-estra-1,3,5(10)-triene-3-carboxylic acid or a salt thereof.

17β-(N-t-butylcarboxamide)-estra-1,3,5(10)-triene-3-carboxylic acid or a salt thereof, 17β-(N,N-diisopropylcarboxamide)-estra-1,3,5(10)-triene-3-sulfonic acid or a salt thereof, 20-α-(hydroxymethyl)-A-nor-5-α-pregn-1-ene-2-carboxylic acid or a salt thereof, 17β-(N-t-butylcarboxamide)-estra-1,3,5(10)-triene-3-sulfonic acid or a salt thereof, 17β-(N,N-diisopropylcarboxamide)estra-1,3,5(10)-triene-3-phosphonic acid or a salt thereof, 17β-(N-t-butylcarboxamide)-estra-1,3,5(10)-triene-3-phosphonic acid or a salt thereof, 17β-(N,N-diisopropylcarboxamide)estra-1,3,5(10-triene-3-phosphinic acid or a salt thereof, 17β-(N-t-butylcarboxamide)-estra-1;3,5(10)-triene-3-phosphinic acid or a salt thereof, 17β-(N-t-butylcarboxamide)-androst-3,5-diene-3-phosphinic acid or a salt thereof, 17β-(N,N-diisopropylcarboxamide)-androst-3,5-diene-3-phosphinic acid or a salt thereof, 17β-(N-t-butylcarboxamide)-androst-3,5-diene-3-phosphonic acid or a salt thereof, 17β-(N,N-diisopropylcarboxamide)-androst-3,5-diene-3-phosphonic acid or a salt thereof, (E)-17β-(N,N-diisopropylcarboxamide)-androst-4-ene-3-ylidene-acetic acid, 17β-(N,N-diisopropylcarboxamide)-androst-3,5-diene-3-acetic acid, (Z)-17β-(N,N-diisopropylcarboxamide)-androst-4-ene-3-ylidene-acetic acid, 17β-(N,N-diisopropylcarboxamide)-5α-androst-2-ene-3-acetic acid, (Z)-17β-(N,N-diisopropylcarboxamide)-5α-androst-3-ylidene-acetic acid, 17β-(N,N-diisopropylcarboxamide)-5α-androst-3-ene-3-acetic acid, and 17β-(N-t-butylcarboxamide)-5α-androst-2-ene-3-acetic acid.

Persons skilled in the art can readily determine if a compound is a steriod 5-α-reductase inhibitor by known methods. All such compounds are included within the scope of this invention.

Because steroid 5-α-reductase inhibitors decrease the size of prostate tumors, they have therapeutic utility in treating prostate adenocarcinoma.

17β-(N-t-butylcarboxamide)-androst-3,5-diene-3-carboxylic acid (compound A) was tested for its in vivo potency in treating human prostatic cancer.

To perform experiments on the human prostatic cancer model, a total of 80 nude mice were used. Each of these animals was inoculated in the flank with PC-82 human prostatic cancer and allowed to go untreated until the tumors were approx. 0.5 $cc^3$ in size (approx. 50 days after inoculation). After this period, 60 of the 80 animals were castrated. A 1 cm long tertosterone filled silastic capsule was implanted subcutaneously in the flank of 20 of the castrated animals and a 2 cm long dihydrotestosterone filled silastic capsule was implanted subcutaneously in the flank of 20 of the castrated animals. The 80 animals were set up in 8 groups as follows:

GROUP 1—intact rats fed twice a day with vehicle alone (intact controls).

GROUP 2—castrated rats fed twice a day with vehicle and not implanted with testosterone or dihydrotestosterone capsule (castrate controls).

GROUP 3—intact rats fed compound (A) (BID) 50 mg/kg.

GROUP 4—castrated rats fed compound (A) (BID) 50 mg/kg and not implanted with testosterone or dihydrotestosterone capsule.

GROUP 5—castrated rats fed twice a day with vehicle and implanted with testosterone capsule.

GROUP 6—castrated rats fed compound (A) (BID) 50 mg/kg and implanted with testosterone capsule.

GROUP 7—castrated rats fed twice a day with vehicle and implanted with dihydrotesterone capsule.

GROUP 8—castrated rats fed compound (A) (BID) 50 mg/kg and implanted with dihydrotestosterone capsule.

The animals were administered the 5-α-reductase inhibiting compound twice a day (BID) for 5 consecutive weeks. The test compound was dissolved in propylene glycol and diluted in water. Tumor volume was measured by caliper twice a week. At the end of the treatment period blood was collected from the animals and they were sacrificed, the ventral prostrates were excised and weighed and the serum androgen levels were determined by known methods. Ewing at al *Endrocrinology* 113:2004–2009, 1983.

The nude mice treated with compound (A) realized a significant decrease in the size of the implanted PC-82 human prostatic cancer, in addition to other therapeutic effects normally associated with inhibitors of steriod 5-α-reductase. Thus, the administration of asteroid 5-α-reductase inhibiting compound results in a therapeutic effect on human prostatic adenocarcinoma.

The claimed compounds and combinations are incorporated into convenient dosage forms such as capsules, tablets, or injectable preparations. Solid or liquid pharmaceutical carriers are employed. Solid carriers include starch, lactose, calcium sulfate dihydrate, terra alba, sucrose, talc, gelatin, agar, pectin, acacia, magnesium stearate, and stearic acid. Liquid carriers include syrup, peanut oil, olice oil, saline, and water. Similarly, the carrier or diluent may include any prolonged release material, such as glyceryl monostearate or glyceryl distearate, alone or with a wax. The amount of solid carrier varies widely but, preferably, will be from about 25 mg to about 1 g per dosage unit. When a liquid carrier is used, the preparation will be in the form of a syrup, elixir, emulsion, soft gelatin capsule, sterile injectable liquid such as an ampoule, or an aqueous or nonaqueous liquid suspension.

The pharmaceutical preparations are made following conventional techniques of a pharmaceutical chemist involving mixing, granulating, and compressing, when necessary, for tablet forms, or mixing, filling and dissolving the ingredients, as appropriate, to give the desired oral or parenteral products.

Doses of the present compounds and combinations in a pharmaceutical dosage unit as described above will be an efficacious, nontoxic quantity selected from the range of 0.1–1000 mg/kg of each active compound, preferably 1–100 mg/kg. The selected dose is administered to a human patient in need of treatment for prostatic adenocarcinoma from 1–6 times daily, orally, by injection or continuously by infusion. Oral dosage units for human administration preferably contain from 1 to 500 mg of active compound. Oral administration, which uses lower dosages is preferred. Parenteral administration, at higher dosages, however, also can be used when safe and convenient for the patient.

The method of this invention of treating prostatic adenocarcinoma comprises administering to a subject in need thereof an effective amount of asteroid 5-α-reductase inhibiting, compound.

Following are the results of testing the compounds of this invention:

TABLE I

The effect of 17β-(N-t-butylcarboxamide)-androst-3,5-diene-3-carboxylic acid (compound A) on inhibiting the growth of PC-82 Human Prostatic adenocarcinoma.

TABLE II

| INGREDIENTS | AMOUNTS |
| --- | --- |
| 17β-(N-t-butylcarboxamide)-androst-3,5-diene-3-carboxylic acid | 100 mg |
| Magnesium stearate | 5 mg |
| Lactose | 75 mg |

EXAMPLE II

The sucrose, calcium sulfate dihydrate and claimed compound shown in Table III below, are mixed and granulated in the proportions shown with a 10% gelatin solution. The wet granules are screened, dried, mixed with the starch, talc and stearic acid, screened and compressed into a tablet.

TABLE I

| | Treatment | Tumor volume (cm$^3$) at identical weeks of treatment | | | | | |
| --- | --- | --- | --- | --- | --- | --- | --- |
| Group No. | (N-6 rats/group) | 0 | 1 | 2 | 3 | 4 | 5 |
| Group 1 | Non-intact Control | 0.59 ± 0.06 (100)$^b$ | 0.71 ± 0.24 (120) | 0.87 ± 0.19 (147) | 1.18 ± 0.20 (200) | 1.28 ± 0.18 (217) | 1.55 ± 0.31 (263) |
| Group 2 | Castrated | 0.64 ± 0.07 (100) | 0.56 ± 0.11 (88) | 0.44 ± 0.09 (69) | 0.42 ± 0.15 (66) | 0.25 ± 0.16 (39) | 0.27 ± 0.10 (42) |
| Group 3 | Intact + compound A | 0.50 ± 0.04 (100) | 0.45 ± 0.05$^a$ (90) | 0.40 ± 0.04$^a$ (80) | 0.38 ± 0.07$^a$ (76) | 0.36 ± 0.03$^a$ (72) | 0.34 ± 0.06$^a$ (68) |
| Group 4 | Castrated + compound A | 0.62 ± 0.10 (100) | 0.51 ± 0.11 (82) | 0.35 ± 0.09 (56) | 0.30 ± 0.10 (48) | 0.28 ± 0.07 (45) | 0.29 ± 0.05 (47) |
| Group 5 | Castrated + testosterone implant | 0.48 ± 0.12 (106) | 0.69 ± 0.07 (143) | 0.78 ± 0.14 (162) | 1.12 ± 0.15 (233) | 1.32 ± 0.19 (275) | 1.60 ± 0.43 (333) |
| Group 6 | Castrated + testosterone implant + compound A | 0.55 ± 0.17 (100) | 0.52 ± 0.10 (95) | 0.45 ± 0.09 (82) | 0.40 ± 0.11 (73) | 0.35 ± 0.17 (64) | 0.38 ± 0.13 (69) |
| Group 7 | Castrated + DHT implant | 0.62 ± 0.10 (100) | 0.74 ± 0.07 (119) | 0.93 ± 0.12 (150) | 1.24 ± 0.22 (200) | 1.42 ± 0.31 (229) | 1.78 ± 0.32 (287) |
| Group 8 | Castrated + DHT implant + compound A | 0.49 ± 0.09 (100) | 0.65 ± 0.11 (133) | 0.87 ± 0.13 (177) | 1.05 ± 0.19 (214) | 1.32 ± 0.35 (269) | 1.72 ± 0.28 (351) |

$^a$Statistically significant
$^b$Values in parentheses are the relative percentages versus the starting values for each group at time 0.

The data in the above table demonstrates the therapeutic effect of steroid 5-α-reductase inhibitors on human prostatic adenocaroinoma.

The following examples illustrate preparation of the claimed pharmaceutical compositions containing steroid 5-α-reductase inhibitors. The examples are not intended to limit the scope of the invention as defined herein above and as claimed below.

EXAMPLE 1

An oral dosage form for administering the claimed compounds is produced by screening, mixing and filling into hard gelatin capsules the ingredients in the proportions shown in table II below.

TABLE III

| INGREDIENTS | AMOUNTS |
| --- | --- |
| 17β-(N-t-butylcarboxamide)-androst-3,5-diene-3-carboxylic acid | 100 mg |
| Calcium sulfate dihydrate | 150 mg |
| Sucrose | 20 mg |
| Starch | 10 mg |
| Talc | 5 mg |
| Stearic Acid | 3 mg |

EXAMPLE III

17β-(N-t-butylcarboxamide)-androst-3,5-diene-3-carboxylic acid (1.0 g) is dissolved in 20 g of soybean oil and emulsified by mixing with 1.2 g of egg phospholipid and enough water to bring the final volume to 100 ml. The formed interlipid formulation is suitable for intravenous administration.

While the preferred embodiments of the invention are illustrated by the above, it is to be understood that the invention is not limited to the precise instructions herein disclosed and that the right to all modifications coming with the scope of the following claims is reserved.

What is claimed is:

1. A method of treating human prostatic adenocarcinoma which comprises administering to a subject in need thereof an oral dosage unit containing from about 1 mg. to about 500 mg. of a steroid 5-α-reductase inhibiting compound from 1–6 times during a twenty four hour period.

2. The method of claim 1 in which the steroid 5-α-reductase inhibiting compound is 17β-(N-t-butylcarboxamide)-androst-3,5-diene-3-carboxylic acid.

* * * * *